United States Patent [19]

Hirose et al.

[11] Patent Number: 5,464,772
[45] Date of Patent: Nov. 7, 1995

[54] **PROCESS FOR PRODUCING OPTICALLY ACTIVE HALOGEN-CONTAINING ALCOHOLS USING LIPASE AY-120 FROM *CANDIDA RUGOSA***

[75] Inventors: Katutoshi Hirose; Yoshihiro Takagi; Toshihiko Otomatsu, all of Kobe; Yoshiichi Suzuki, Tokyo, all of Japan

[73] Assignee: Showa Shell Sekiyu Kabushiki Kaisha, Tokyo, Japan

[21] Appl. No.: 46,181

[22] Filed: Apr. 14, 1993

[30] Foreign Application Priority Data

Apr. 15, 1992 [JP] Japan ................. 4-121209

[51] Int. Cl.⁶ ................................. C12P 41/00
[52] U.S. Cl. ................. 435/280; 435/156; 435/157
[58] Field of Search ..................... 435/280, 156, 435/157

[56] References Cited

U.S. PATENT DOCUMENTS

| | | | |
|---|---|---|---|
| 4,764,464 | 8/1988 | Zemel | 435/136 |
| 4,929,760 | 5/1990 | Kitazume et al. | 568/308 |
| 4,996,158 | 2/1991 | Oda et al. | 435/280 |
| 5,047,346 | 9/1991 | Kitazume et al. | 435/280 |

FOREIGN PATENT DOCUMENTS

| | | |
|---|---|---|
| 0549872 | 7/1983 | European Pat. Off. . |
| 0288994 | 11/1988 | European Pat. Off. . |
| 0334966 | 10/1989 | European Pat. Off. . |
| 0529085 | 3/1993 | European Pat. Off. . |
| 1-233244 | 9/1989 | Japan . |
| 1-233243 | 9/1989 | Japan . |
| 2-282340 | 9/1990 | Japan . |

OTHER PUBLICATIONS

Hills M et al, Biochemica Biophys Acta 1042:237–40 (1990).
Okumura S et al, Biochimica Biophys Acta 575:156–65 (1979).
Carrea G, Trends in Biotech. 2:102–106 (1984).
Kazlauskas R et al, J. Org Chem 56:2656–65 (1991).
Kalaritis P et al, J. Org Chem. 55:812–15 (1990).
Guanti G et al, Tetra Lett 27:4639–42 (1986).
Atcc Catalogue p. 17 (1990).
Dernoncour R et al, Tet Lett 28:4661–64 (1987).
Amano Catalog of Lipases and Esterases.
Chemical Abstracts, vol. 107, No. 7, 17 Aug. 1987, Abstract No. 57471m, p. 603.
Chemical Abstracts, vol. 114, No. 25, 24 Jun. 1991, Abstract No. 245958u, p. 641.
Chemical Abstracts, vol. 111, No. 11, 11 Sep. 1989, Abstract No. 95626f, p. 602.
Chemical Abstracts, vol. 107, No. 11, 14 Sep. 1987, Abstract No. 95238y, p. 569.
Boutelje J et al Bioorganic chemistry 16:364–375 (1988).
Drueckhammer D et al J. Org. Chem. 53:1607–1611 (1988).
Chenevert R et al Can. J. Chem. vol. 66: 1219–1222 (1988).

*Primary Examiner*—Marian C. Knode
*Assistant Examiner*—S. Saucier
*Attorney, Agent, or Firm*—Cushman, Darby & Cushman

[57] ABSTRACT

A process for producing an optically active halogen-containing alcohol having a high optical purity and represented by the following formula [I]

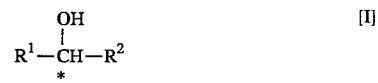

wherein $R^1$ is a halogen substituted alkyl group, $R^2$ is a group selected from the group consisting of a substituted or unsubstituted alkyl group, alkene group, or alkyne group, and a substituted or unsubstituted phenyl group, and C having an asterisk indicates an asymmetric atom, is disclosed which process comprises subjecting a halogenated alkyl ester of a carboxylic acid represented by the following formula [II]

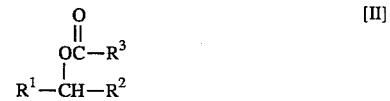

wherein $R^1$ and $R^2$ are the same as mentioned above and $R^3$ is a group selected from the group consisting of a substituted or unsubstituted alkyl group or alkene group, and a substituted or unsubstituted phenyl group, to asymmetric hydrolysis with an enzyme in an aqueous solution system, and the aqueous solution system may contain buffer solution and/or organic solvent.

6 Claims, No Drawings

PROCESS FOR PRODUCING OPTICALLY ACTIVE HALOGEN-CONTAINING ALCOHOLS USING LIPASE AY-120 FROM *CANDIDA RUGOSA*

BACKGROUND OF THE INVENTION

1. Field of the Invention

The present invention relates to a process for producing an optically active halogen-containing alcohol.

2. Description of the Related Art

Optically active halogen-containing alcohols have been produced by an asymmetric synthesis or an optical resolution with a diastereomer. However, it is very difficult to obtain optically active halogen-containing alcohols having a high optical purity and to obtain the alcohols in a large quantity. Thus, few methods have been established as practical ones for producing optically active halogen-containing alcohols.

On the other hand, optical resolution methods using an enzyme have been disclosed in Japanese Unexamined Patent Publication Nos. 2-282,340, 1-233,243, and 1-233,244 all of which have been filed by the present inventors. However, it is still difficult to obtain optically active substances having a high optical purity at a high production yield since the selectivity in the reaction is low. Further, the methods involve several technical problems that the synthesis of the optically active substances in a large quantity at a high reproducibility is difficult since substrates in the reaction are inferior in dispersibility such that the substrates would usually form a heterogeneous system.

As methods for dissolving such problems, attempts have been reported in J. Boutelje et al., Bioorg. Chem., 16, 364 (1988) "A method for the synthesis of cis-N-benzyl-2,5-bismethoxycarbonyl pyridine" and C. H. Wong et al., J. Org. Chem., 53, 1607 (1988) "A method for the synthesis of furylmethyl carbinol" wherein an optical resolution is carried out at a high selectivity by adding an organic solvent in a water system in an asymmetric hydrolysis of an ester with an enzyme.

Further, another attempt has been reported in R. Chenevert et al., Can. J. Chem., 66, 1219 (1988) wherein a buffer solution is used instead of water in order to have a high selectivity in the asymmetric hydrolysis of chlorophenoxy propionate.

However, no report has been published in which such attempts mentioned above were applied for the preparation of a halogen-containing alcohol.

SUMMARY OF THE INVENTION

An object of the present invention is to provide a process for producing an optically active halogen-containing alcohol by an optical resolution through an asymmetric hydrolysis of an alkyl ester of carboxylic acid with an enzyme in an aqueous solution system.

A further object of the present invention is to provide a process for producing an optically active substance having a high optical purity at a high production yield with an excellent reproducibility by adding a specific organic solvent and/or a buffer solution or composition in an aqueous solution system to uniformly disperse a substrate in an optical resolution through asymmetric hydrolysis of a halogenated alkyl ester of a carboxylic acid with an enzyme.

A still further object of the present invention will be apparent to those skilled in the art from the following detailed description and appended claims.

The present invention relates to a process for producing an optically active halogen-containing alcohol represented by the following formula [I]

wherein $R^1$ is a halogen substituted alkyl group, $R^2$ is selected from the group consisting of a substituted or unsubstituted alkyl group, alkene group, or alkyne group, and a substituted or unsubstituted phenyl group, and C having an asterisk indicates an asymmetric atom, which process comprises subjecting a halogenated alkyl ester of a carboxylic acid represented by the following formula [II]

wherein $R^1$ and $R^2$ are the same as mentioned above and $R^3$ is a group selected from the group consisting of a substituted or unsubstituted alkyl group or alkene group, and a substituted or unsubstituted phenyl group, to asymmetric hydrolysis with an enzyme in an aqueous solution system.

DESCRIPTION OF THE PREFERRED EMBODIMENTS

The aqueous solution system may be added with an organic solvent and/or a buffer solution or composition.

The $R^1$ in the formulas [I] and [II] which is a halogen substituted alkyl group includes $CF_3$, $CCl_3$, $CF_3CF_2$, $CF_3CCl_2$, and $CF_3CH_2$.

The $R^2$ in the formula [I] and [II] includes $C_nH_{2n+1}$ (wherein n is an integer of 2 to 16), as an alkyl group, such as $C_6H_{13}$, $C_8H_{17}$, and $C_{10}H_{21}$; $C_nH_{2n-1}$ (wherein n is an integer of 2 to 16), as an alkene group, preferably in particular an alkene group having a double bond at its end; $C_nH_{2n-3}$ (wherein n is an integer of 2 to 16), as an alkyne group, preferably in particular an alkyne group having a triple bond at its end; a substituted alkyl group such as phenyl substituted methyl group and phenyl substituted ethyl group; and a substituted or unsubstituted phenyl group such as phenyl group, methoxyphenyl group, and p-fluorophenyl group.

The $R^3$ in the formula [II] includes, as an alkyl group of $C_1$–$C_{18}$, for example, a linear alkyl group such as $CH_3$, $C_2H_5$, and $C_7H_{15}$, and a branched alkyl group such as t-butyl group; a substituted alkyl group such as $CH_2Cl$, $CH_2Br$, benzyl group, and styryl group; an alkene group such as $-CH=CHCH_3$, $-C(CH_3)=CH_2$, and $-CH=CHCH=CHCH_3$; and a substituted or unsubstituted phenyl group such as phenyl group and nitrophenyl group.

As the enzyme used in the present invention, there may be mentioned a lipase derived from a microorganism belong to a genus such as Pseudomonas, Geotrichum, Chromobacterium, or Mucor; a lipase derived from a yeast belonging to a genus such as Candida, Porcine Pancreas Lipase, and other enzymes such as Pig Liver Esterase. However, the enzyme is not restricted to such enzymes as mentioned above as long as it can be used for the purpose of optical resolution in the present invention.

The temperature of a reaction system when an enzyme is reacted may be in a range in which an enzyme to be used can not be deactivated and it is usually in a range from −20° C. to 60° C.

While the pH in a reaction system when an enzyme is reacted will be varied according to a particular enzyme to be used, the pH may be in a range in which the enzyme can not be deactivated.

The organic solvent used in the present invention includes an alcohol, ketone, ether, ester, amide, sulfoxide, and nitrile. Specific examples of the solvent includes methanol, ethanol, n-propanol, iso-propanol, n-butanol, t-butanol, ethylene glycol, glycerin, acetone, tetrahydrofuran, ethylacetate, dioxane, acetonitrile, formamide, dimethyl formamide, dimethyl sulfoxide (DMSO), dimethyl acetamide, 1,3-dimethyl-2-imidazolidinone (DMI), N-methylpyrrolidone, and hexamethylphosphoric triamide (HMPA). However, the organic solvent is not restricted to the solvents mentioned above.

The amount of the organic solvent to be used is not specifically restricted as long as the solvent will not deactivate the enzyme to be used, but it is preferably from 0.1% to 70% by volume ratio to a culture solution.

Further, in order to stabilize a reaction system, it is preferable to add a buffer solution or buffer composition to the reaction system. The buffer solution or composition may be an inorganic solution or composition such as a phosphate buffer, or an organic solution or composition containing tris(hydroxymethyl)aminomethane, triethanolamine, or imidazole.

According to the present invention, a novel process is provided in which an optically active halogen-containing alcohol can be produced by utilizing an enzyme.

EXAMPLES

Now, the present invention will be described in further detail in reference to Examples. However, it should be understood that the present invention is by no means restricted by such specific Examples.

Determinations of the reaction ratio in terms of conversion and optical purity used in Examples were conducted by the methods as follows: Reaction ratio:

The reaction ratio of hydrolysis was determined by sampling a part of a reaction liquid, subjecting it to extraction with an ether, and analyzing about 3 μl of the ether layer by a gas chromatography under the following conditions:
[Conditions for gas chromatography]
  Column: SE-30
  Inlet temperature: 250° C.
  Column temperature: 100° C.
  Detector: FID
Optical purity:
  Weighing about 0.5 mg of a sample alcohol, dissolving it in 0.5 ml of a dried toluene, adding about 0.5 mg of grinded 3,5-dinitrophenyl isocyanate to the toluene, and then adding about 5 to 10 mg of 4-dimethylaminopyridine. After stirring for 1 hour at a temperature of 60° to 70° C., concentrating the resulting mixture at a temperature of 60° to 70° C. Dissolving the residue in about 15 ml of an ether, washing it with 1M-HCl×2, $H_2O$×1, 1M-$NaHCO_3$×2, and saturated aqueous solution of NaCl×1 in this order, and drying with anhydrous sodium sulfate. Then, analyzing the ether layer of about 8 ml by a high pressure liquid chromatography (HPLC) under the following conditions:

[Conditions for HPLC]
  Column: SUMICHIRAL OA-4000
  Eluate: n-hexane:$CH_2Cl_2$:IPA=50:30:1
  Flow rate: 1 ml/min
  Detection wave length: 254 nm
  Note: IPA is an abbreviation for isopropanol.

Example 1

In 55 ml of water were added 1.67 g of 1,1,1-trifluoro-2-octylacetate and 0.75 g of lipase OF-360 (Meito Sangyo, Japan) derived from a genus of Candida, and the resulting mixture was subjected to reaction for 40 hours at a temperature of 40° C. at a pH of 6.8 with sufficient stirring. The reaction was conducted while checking the conversion of the octylacetate into an alcohol with a gas chromatography. The reaction was terminated by separating the lipase from the reaction liquid by suction filtration at a conversion of 43.2%. After the concentration of the filtrate, the alcohol thus resulted was separated and purified with a silica gel chromatography using benzene, and further subjected to distillation to obtain 0.41 g of 1,1,1-trifluoro-2-octanol.

As a result of analysis by a high pressure liquid chromatography with a 3,5-dinitrophenyl isocyanate derivative, the alcohol was found to have (R)-form having an optical purity of 89.5% ee. E value which shows the selectivity between enantiomers was 36.8.

Example 2

In 50 ml of water were added 1.67 g of 1,1,1-trifluoro-2-octylacetate and 0.75 g of lipase of 360. Then, 5 ml of methanol was further added as organic solvent to the resulting mixture and subjected to reaction in the same manner as in Example 1. The optically active 1,1,1-trifluoro-2-octanol in amount of 0.35 g which was obtained in a reaction time of 48 hours and a conversion of 37.2% had an optical purity of 90.1% ee and an E value of 89.4.

Example 3

Example 2 was repeated except that n-butanol was used as organic solvent instead of methanol. The optically active 1,1,1-trifluoro-2-octanol in amount of 0.41 g which was obtained in a reaction time of 22 hours and a conversion of 42.0% had an optical purity of 94.6% ee and an E value of 74.2.

Examples 4 to 17

Example 3 was repeated except that an organic solvent shown in Table 1 was used instead of n-butanol. The results thus obtained are shown in Table 1 together with the results in Examples 1 to 3.

The following conditions were used in common in Examples 1 through 17:
  1,1,1-trifluoro-2-octylacetate: 1.67 g
  Lipase OF-360: 0.75 g
  Water: 50 ml
  Organic solvent: 5 ml
  pH of reaction system: 6.8
  Temperature of reaction system: 40° C.
  In Example 1, 55 ml of water was added without using organic solvent.

TABLE 1

| Example | Organic solvent | Reaction time (hr) | Conversion (%) | Yield (g) | Optical purity (% ee) | E value |
|---|---|---|---|---|---|---|
| 1 | nil | 40 | 43.2 | 0.41 | 89.5 | 36.8 |
| 2 | Methanol | 48 | 37.2 | 0.35 | 96.1 | 89.4 |
| 3 | n-butanol | 22 | 42.0 | 0.41 | 94.6 | 74.2 |
| 4 | t-butanol | 17 | 36.6 | 0.33 | 96.7 | 105 |
| 5 | Ethylene glycol | 23 | 41.0 | 0.38 | 95.4 | 84.8 |
| 6 | Glycerin | 21.5 | 38.7 | 0.37 | 93.3 | 52.4 |
| 7 | Acetone | 44 | 32.3 | 0.29 | 96.6 | 91.3 |
| 8 | Tetrahydrofuran | 38 | 44.5 | 0.43 | 96.2 | 121 |
| 9 | Dioxane | 61 | 35.7 | 0.34 | 96.6 | 91.3 |
| 10 | Acetonitrile | 74 | 38.5 | 0.35 | 96.5 | 104 |
| 11 | Formamide | 13.5 | 39.0 | 0.36 | 95.8 | 87.3 |
| 12 | Dimethyl formamide | 70 | 44.8 | 0.44 | 95.4 | 100 |
| 13 | Dimethyl sulfoxide | 38 | 42.9 | 0.40 | 96.3 | 116 |
| 14 | Dimethyl acetamide | 45.5 | 43.3 | 0.39 | 96.2 | 114 |
| 15 | DMI | 52 | 34.7 | 0.31 | 97.0 | 110 |
| 16 | N-methyl pyrrolidone | 48 | 35.8 | 0.37 | 97.4 | 131 |
| 17 | HMPA | 40 | 38.4 | 0.40 | 97.9 | 176 |

The following Examples 18 through 27 were conducted to confirm the effect of the addition of hexamethylphosphoric triamide (HMPA) as organic solvent.

Example 18

In 25.05 ml of water were added 1.67 g of 1,1,1-trifluoro-2-octylacetate and 0.334 g of lipase OF-360, and the resulting mixture was subjected to reaction for 61 hours at a temperature of 40° C. at a pH of 6.8 with sufficient stirring. The reaction was conducted while checking the conversion of the octylacetate into an alcohol with a gas chromatography. The reaction was terminated by separating the lipase from the reaction liquid by suction filtration at a conversion of 36.0%. After the concentration of the filtrate, the alcohol thus resulted was separated and purified with a silica gel chromatography using benzene, and further subjected to distillation to obtain 0.31 g of 1,1,1-trifluoro-2-octanol.

As a result of analysis by a high pressure liquid chromatography with a 3,5-dinitrophenyl isocyanate derivative, the alcohol was found to have (R)-form having an optical purity of 95.6 %ee. E value which shows the selectivity between enantiomers was 76.3.

Example 19

In 21.3 ml of water were added 1.67 g of 1,1,1-trifluoro-2-octylacetate and 0.334 g of lipase OF-360. Then, 3.76 ml of HMPA was further added as organic solvent to the resulting mixture and subjected to reaction in the same manner as in Example 18. The optically active 1,1,1-trifluoro-2-octanol in amount of 0.33 g which was obtained in a reaction time of 58 hours and a conversion of 33.7% had an optical purity of 97.5% ee and an E value of 129.

Example 20

Example 18 was repeated except that 25 ml of an aqueous buffer solution (0.1M-$KH_2PO_4$-0.1N-NaOH) was used instead of water. The optically active 1,1,1-trifluoro-2-octanol in amount of 0.36 g which was obtained in a reaction time of 59 hours and a conversion of 38.7% had an optical purity of 95.8% ee and an E value of 86.5.

Example 21

Example 19 was repeated except that 21.3 ml of an aqueous buffer solution (0.1M-$KH_2PO_4$-0.1N-NaOH) was used instead of water. The optically active 1,1,1-trifluoro-2-octanol in amount of 0.35 g which was obtained in a reaction time of 37 hours and a conversion of 35.6% had an optical purity of 98.1% ee and an E value of 180.

Examples 22 to 27

In Examples 22, 24, and 26, the reaction was conducted in the same manner as in Example 20 except that an aqueous buffer solution shown in Table 2 was used instead of an aqueous phosphate buffer solution.

In Examples 23, 25, and 27, the reaction was conducted in the same manner as in Example 21 except that an aqueous buffer solution shown in Table 2 was used instead of an aqueous phosphate buffer solution.

The results thus obtained are shown in Table 2 together with the results in Examples 18 to 21.

The following conditions were used in common in Examples 18 through 27:

1,1,1-trifluoro-2-octylacetate: 1.67 g

Lipase OF-360: 0.334 g pH of reaction system: 6.8

Temperature of reaction system: 40° C.

Further, the amounts of water, the aqueous solution, and the organic solvent added in these Examples were as follows:

In the cases when only water or the aqueous solution was used:
   Water or aqueous solution: 25.05 ml
In the cases where the aqueous solution and the organic solvent were used:
   Aqueous solution: 21.30 ml
   Organic solvent: 3.76 ml

TABLE 2

(Effect of addition of HMPA)

| Example | Aqueous solution system | Reaction conditions | | | Alcohol | | |
|---|---|---|---|---|---|---|---|
| | | HMPA | Reaction time (hr) | Conversion (%) | Yield (g) | Optical purity (% ee) | E value |
| 18 | Water | — | 61 | 36.0 | 0.31 | 95.6 | 76.3 |
| 19 | Water | used | 58 | 33.7 | 0.33 | 97.5 | 129 |
| 20 | 0.1M-$KH_2PO_4$—0.1N—NaOH | — | 59 | 38.7 | 0.36 | 95.8 | 86.5 |
| 21 | 0.1M- | used | 37 | 35.6 | 0.35 | 98.1 | 180 |

TABLE 2-continued (Effect of addition of HMPA)

| | Reaction conditions | | | | Alcohol | | |
|---|---|---|---|---|---|---|---|
| Example | Aqueous solution system | HMPA | Reaction time (hr) | Conversion (%) | Yield (g) | Optical purity (% ee) | E value |
| 22 | KH$_2$PO$_4$—0.1N—NaOH 0.1M-tris-0.1N—HCl | — | 31 | 31.9 | 0.30 | 96.8 | 96.4 |
| 23 | 0.1M-tris-0.1N—HCl | used | 28 | 40.4 | 0.38 | 97.5 | 158 |
| 24 | 0.2M-triethanol amine-0.1N—HCl | — | 44 | 40.5 | 0.41 | 94.9 | 74.6 |
| 25 | 0.2M-triethanol amine-0.1N—HCl | used | 29 | 34.5 | 0.33 | 97.3 | 122 |
| 26 | 0.2M-imidazole-0.1N—HCl | — | 39 | 42.9 | 0.37 | 96.2 | 112 |
| 27 | 0.2M-imidazole-0.1N—HCl | used | 50 | 38.0 | 0.36 | 97.3 | 134 |

The following Examples 28 through 31 were conducted to confirm the effect of the mixing ratio of an organic solvent.

Example 28

In 25.05 ml of a phosphate buffer (0.1M-KH$_2$PO$_4$-0.1N-NaOH) containing 0.1% of HMPA were added 1.67 g of 1,1,1-trifluoro-2-octylacetate and 0.334 g of lipase OF-360, and the resulting mixture was subjected to reaction for 30 hours at a temperature of 40° C. at a pH of 6.8 with sufficient stirring. The reaction was conducted while checking the conversion of the octylacetate into an alcohol with a gas chromatography. The reaction was terminated by separating the lipase from the reaction liquid by suction filtration at a conversion of 42.9%. After the concentration of the filtrate, the alcohol thus resulted was separated and purified with a silica gel chromatography using benzene, and further subjected to distillation to obtain 0.39 g of 1,1,1-trifluoro-2-octanol.

As a result of analysis by a high pressure liquid chromatography with a 3,5-dinitrophenyl isocyanate derivative, the alcohol was found to have (R)-form having an optical purity of 96.3% ee. E value which shows the selectivity between enantiomers was 113.

Example 29

In 25.05 ml of a phosphate buffer (0.1M-KH$_2$PO$_4$-0.1N-NaOH) containing 1.0% of HMPA were added 1.67 g of 1,1,1-trifluoro-2-octylacetate and 0.334 g of lipase OF-360, and the reaction was conducted in the same manner as in Example 28. The optically active 1,1,1-trifluoro-2-octanol in amount of 0.33 g which was obtained in reaction time of 31 hours and a conversion of 37.2% had an optical purity of 97.1% ee and an E value of 122.

Examples 30 and 31

Examples 28 was repeated except that the mixing ratio of HMPA was changed in Example 30 as shown in Table 3 and DMSO was used in Example 31 instead of HMPA as shown in said Table. The results are shown in Table 3 together with the results in Example 28, 29, and 21 for the convenience of comparison.

The following conditions were used in common in

Examples 28 through 31:

1,1,1-trifluoro-2-octylacetate: 1.67 g

Lipase OF-360: 0.334 g

Total amount of 0.1M-KH$_2$PO$_4$-0.1 N-NaOH and HMPA (or DMSO): 25.05 ml pH of reaction system: 6.8

Temperature of reaction system: 40° C.

TABLE 3

(Effect of mixing ratio of HMPA or DMSO)

| | | Reaction conditions | | | Alcohol | |
|---|---|---|---|---|---|---|
| Example | HMPA (%) | Reaction time (hr) | Conversion (%) | Yield (g) | Optical purity (% ee) | E value |
| 28 | 0.1 | 30 | 42.9 | 0.39 | 96.3 | 113 |
| 29 | 1.0 | 31 | 37.2 | 0.33 | 97.1 | 122 |
| 21 | 15 | 37 | 35.6 | 0.35 | 98.1 | 180 |
| 30 | 30 | 90 | 10.6 | 0.08 | 98.0 | 111 |
| 31 | 50* | 83 | 5.2 | 0.04 | 96.2 | 54.4 |

*DMSO

The following Examples 32 through 35 were conducted to confirm the effect of reaction temperature.

Example 32

In a mixture of 21.3 ml of a phosphate buffer (0.1M-KH$_2$PO$_4$-0.1N-NaOH) and 3.76 ml of HMPA as organic solvent were added 1.67 g of 1,1,1-trifluoro-2-octylacetate and 0.334 g of lipase OF-360, and the resulting mixture was subjected to reaction for 36 hours at a temperature of 20° C. at a pH of 6.8 with sufficient stirring. The reaction was conducted while checking the conversion of the octylacetate into an alcohol with a gas chromatography. The reaction was terminated by separating the lipase from the reaction liquid by suction filtration at a conversion of 37.8%. After the concentration of the filtrate, the alcohol thus resulted was separated and purified with a silica gel chromatography using benzene, and further subjected to distillation to obtain 0.38 g of 1,1,1-trifluoro-2-octanol.

As a result of analysis by a high pressure liquid chromatography with a 3,5-dinitrophenyl isocyanate derivative, the alcohol was found to have (R)-form having an optical purity of 97.6% ee. E value which shows the selectivity between enantiomers was 151.

Example 33

In a mixture of 21.3 ml of a phosphate buffer (0.1M-KH$_2$PO$_4$-0.1N-NaOH) and 3.76 ml of HMPA as organic solvent were added 1.67 g of 1,1,1-trifluoro-2-octylacetate and 0.334 g of lipase OF-360, and the resulting mixture was subjected to reaction in the same manner as in Example 32. The optically active 1,1,1-trifluoro-2-octylacetate in an amount of 0.36 g which was obtained in a reaction time of 32 hours and a conversion of 39.4% had an optical purity of 96.9 % ee and an E value of 122.

Examples 34 and 35

Example 32 was repeated except that the reaction temperature was varied as shown in Table 4. The results thus obtained are shown in Table 4 together with the results in Examples 32, 33, and 21 for the convenience of comparison.

The following conditions were used in common in Examples 32 through 35:

1,1,1-trifluoro-2-octyl acetate: 1.67 g

Lipase OF-360: 0.334 g 0.1M-$KH_2PO_4$-0.1N-NaOH Aqueous solution: 21.3 ml:

HMPA: 3.76 ml pH of reaction system: 6.8

TABLE 4

(Effect of reaction temperature)

| | Reaction conditions | | | Alcohol | | |
|---|---|---|---|---|---|---|
| Example | Temperature (°C.) | Reaction time (hr) | Conversion (%) | Yield (g) | Optical purity (% ee) | E value |
| 32 | 2 | 36 | 37.8 | 0.38 | 97.6 | 151 |
| 33 | 20 | 32 | 39.4 | 0.36 | 96.9 | 122 |
| 21 | 40 | 37 | 35.6 | 0.35 | 98.1 | 180 |
| 34 | 43 | 49 | 20.9 | 0.16 | 98.4 | 160 |
| 35 | 50 | 46 | 3.2 | 0.03 | 96.5 | 58 |

Example 36

In 25.05 ml of a phosphate buffer (0.1M-$KH_2PO_4$-0.1N-NaOH) were added 1.46 g of 1,1,1-trifluoro-2-hexylacetate and 0.134 g of lipase AY-120 (Amano Seiyaku, Amano Pharmaceutical Co., Ltd., Japan), derived from a genus of Candida rugosa, and the resulting mixture was subjected to reaction for 38 hours at a temperature of 40° C. at a pH of 6.8 with sufficient stirring. The reaction was conducted while checking the conversion of the hexylacetate into an alcohol with a gas chromatography. The reaction was terminated by separating the lipase from the reaction liquid by suction filtration at a conversion of 40.9%. After the concentration of the filtrate, the alcohol thus resulted was separated and purified with a silica gel chromatography using benzene to obtain 1,1,1-trifluoro-2-heptanol.

As a result of analysis by a high pressure liquid chromatography with a 3,5-dinitrophenyl isocyanate derivative, the alcohol was found to have (R)-form having an optical purity of 95.3% ee. E value which shows the selectivity between enantiomers was 82.6.

Example 37

In 22.55 ml of a phosphate buffer (0.1M-$KH_2PO_4$-0.1N-NaOH) were added 1.46 g of 1,1,1-trifluoro-2-hexylacetate and 0.134 g of lipase AY-120, and 2.5 ml of HMPA was further added as organic solvent, and the mixture was subjected to reaction in the same manner as in Example 36. The optically active alcohol which was obtained in reaction time of 41 hours and a conversion of 39.7% had an optical purity of 96.1% ee and an E value of 96.6.

Examples 38 to 47

As a raw material, an ester represented by the following formula [III]:

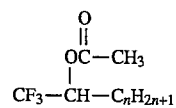

wherein n is an integer of 5 to 9, was used in an amount as shown in Table 5 instead of 1,1,1-trifluoro-2-hexylacetate, and the reaction was conducted in the same way as in Example 36 when an organic solvent was not used; or in the same manner as in Example 37 when HMPA was used as organic solvent; provided that the reaction time and conversion were as shown in Table 5. The optically active alcohols thus obtained were found to have (R)-form, and an optical purity and E value are shown in Table 5.

In Table 5, the results in Examples 36 and 37 are also shown.

The following conditions were used in common in Examples 36 through 47:

Lipase AY-120: 0.134 g pH of reaction system: 6.8

Temperature of reaction system: 40° C.

Further, the amount of the buffer solution and organic solvent added in these Examples were as follows:

In the cases when only a phosphate buffer was used:
Phosphate buffer: 25.05 ml

In the cases when a phosphate buffer and an organic solvent were used:

Phosphate buffer: 22.55 ml

Organic solvent (HMPA): 2.5 ml

TABLE 5

| | Ester as raw material | | | Reaction time | Conversion | Optical purity | E |
|---|---|---|---|---|---|---|---|
| Example | n | (g) | HMPA | (hr) | (%) | (% ee) | value |
| 36 | 4 | 1.46 | — | 38 | 40.9 | 95.3 | 82.6 |
| 37 | 4 | 1.46 | used | 47 | 39.7 | 96.1 | 96.6 |
| 38 | 5 | 1.57 | — | 47 | 36.6 | 96.2 | 90.4 |
| 39 | 5 | 1.57 | used | 44 | 28.0 | 98.6 | 206.8 |
| 40 | 6 | 1.67 | — | 29 | 35.3 | 96.4 | 92.4 |
| 41 | 6 | 1.67 | used | 45 | 32.1 | 98.3 | 185.0 |
| 42 | 7 | 1.78 | — | 31 | 35.5 | 95.1 | 67.2 |
| 43 | 7 | 1.78 | used | 39 | 31.4 | 96.7 | 92.3 |
| 44 | 8 | 1.88 | — | 32 | 21.4 | 89.6 | 23.1 |
| 45 | 8 | 1.88 | used | 48 | 19.8 | 96.2 | 65.1 |
| 46 | 9 | 1.98 | — | 47 | 17.3 | 90.5 | 24.1 |
| 47 | 9 | 1.98 | used | 70 | 7.7 | 96.1 | 54.4 |

Example 48

In 50 ml of water were added 1.82 g of 1,1,1-trifluoro-4-phenyl-2-butylacetate and 0.75 g of lipase OF-360, 5 ml of HMPA was further added as organic solvent, and the resulting mixture was subjected to reaction in the same manner as in Example 17. The optically active 1,1,1-trifluoro-4-phenyl-2-butanol in amount of 0.40 g which was obtained in a reaction time of 35 hours and a conversion of 44% had an optical purity of 94.8% ee and an E value of 84.1.

Example 49

In 50 ml of water were added 1.80 g of 1,1,1-trifluoro-4-phenyl-3-butenyl-2-acetate and 0.75 g of lipase OF-360, 5 ml of HMPA was further added, and the resulting mixture was subjected to reaction in the same manner as in Example 17. The optically active 1,1,1-trifluoro-2-hydroxy-4-phenyl-3-butene represented by the following formula

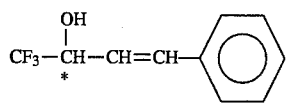

in an amount of 0.23 g which was obtained in a reaction time of 29 hours and a conversion of 25.8% had an optical purity of 61% ee and an E value of 5.1.

Example 50

In 50 ml of water were added 1.61 g of 1,1,1-trifluoro-2-phenylethylacetate and 0.75 g of lipase OF-360, 5 ml of HMPA was further added as organic solvent, and the resulting mixture was subjected to reaction in the same manner as in Example 17. The optically active 1,1,1-trifluoro-2-phenylethyl alcohol in amount of 0.32 g which was obtained in a reaction time of 24 hours and a conversion of 40% had an optical purity of 57% ee and an E value of 0.2.

Example 51

In 50 ml of water were added 1.84 g of 1,1,1-trifluoro-3-decynyl-2-acetate and 0.75 g of lipase MY derived from a genus of Candida (manufactured by Meito Sangyo), 5 ml of HMPA was further added as organic solvent, and the resulting mixture was subjected to reaction in the same manner as in Example 17. The optically active 1,1,1-trifluoro-3-decyn-2-ol represented by the following formula

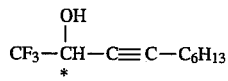

in an amount of 0.30 g which was obtained in a reaction time of 50 hours and a conversion of 33% had an optical purity of 44.8% ee and an E value of 3.3.

Example 52

In 50 ml of water was added 3.18 g of 1,1,1,2,2-pentafluoro-3-undecyl-butanoate and 0.75 g of lipase OF-360, 5 ml of HMPA was further added as organic solvent, and the resulting mixture was subjected to reaction in the same manner as in Example 17. The optically active 1,1,1,2,2-pentafluoro-3-undecanol represented by the following formula

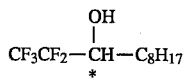

which was obtained in a reaction time of 55 hours and a conversion of 35% had an optical purity of 74% ee and an E value of 9.8.

We claim:

1. A process for producing an optically active halogen-containing alcohol of the formula I

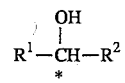

wherein $R^1$ is selected from the group consisting of $CF_3$, $CCl_3$, $CF_3CCl_2$, $CF_3CH_2$ and $CF_3CF_2$, $R^2$ is selected from the group consisting of an alkyl group of $C_2$–$C_{16}$, alkene group of $C_2$–$C_{16}$, alkyne group of $C_2$–$C_{16}$, phenyl group, and alkyl substituted phenyl group, and the C having an asterisk indicates an asymmetric atom, comprising asymmetrically hydrolyzing a halogenated alkyl ester of a carboxylic acid represented by the following formula II

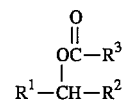

wherein $R^1$ and $R^2$ are the same as mentioned above and $R^3$ is selected from the group consisting of an alkyl group of $C_1$–$C_{18}$, alkene group of $C_1$–$C_{18}$, alkane group of $C_1$–$C_{18}$, phenyl group, and alkyl substituted phenyl group, with lipase AY-120 in an aqueous solution; and purifying said optically active halogen-containing alcohol.

2. The process for producing an optically active halogen-containing alcohol according to claim 1 further comprising adding a buffer solution or buffer composition to the aqueous solution.

3. The process for producing an optically active halogen-containing alcohol according to claim 1, wherein $R_1$ is $CF_3$ and $R_2$ is selected from the group consisting of an alkyl group of $C_2$–$C_{16}$ and alkene group of $C_2$–$C_{16}$, and $R_3$ is methyl.

4. A process for producing an optically active halogen-containing alcohol of the formula I

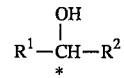

wherein $R^1$ is selected from the group consisting of $CF_3$, $CCl_3$, $CF_3CCl_2$, $CF_3CH_2$ and $CF_3CF_2$, $R^2$ is selected from the group consisting of an alkyl group of $C_2$–$C_{16}$, alkene group of $C_2$–$C_{16}$, alkyne group of $C_2$–$C_{16}$, phenyl group, and alkyl substituted phenyl group, and the C having an asterisk indicates an asymmetric atom, comprising asymmetrically hydrolyzing a halogenated alkyl ester of a carboxylic acid represented by the following formula II

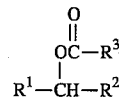

wherein $R^1$ and $R^2$ are the same as mentioned above and $R^3$ is selected from the group consisting of an alkyl group of $C_1$–$C_{18}$, alkene group of $C_1$–$C_{18}$, alkyne group of $C_1$–$C_{18}$, phenyl group, and alkyl substituted phenyl group, with lipase AY-120 from Candida in a mixture of water and at least one organic solvent selected from the group consisting of an alcohol, ketone, amide, sulfoxide and nitrile; and purifying said optically active halogen-containing alcohol.

5. The process for producing an optically active halogen-containing alcohol according to claim 4 further comprising adding a buffer solution or buffer composition to the mixture of water and organic solvent.

6. The process for producing an optically active halogen-containing alcohol according to claim 4, wherein $R_1$ is $CF_3$, $R_2$ is selected from the group consisting of an alkyl group of $C_2$–$C_{16}$ and alkene group of $C_2$–$C_{16}$, and $R_3$ is methyl.

* * * * *